United States Patent
Kortagere

(10) Patent No.: US 9,861,594 B2
(45) Date of Patent: Jan. 9, 2018

(54) TREATMENTS FOR ATTENTION AND COGNITIVE DISORDERS, AND FOR DEMENTIA ASSOCIATED WITH A NEURODEGENERATIVE DISORDER

(71) Applicant: Drexel University, Philadelphia, PA (US)

(72) Inventor: Sandhya Kortagere, Newtown, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/028,654

(22) PCT Filed: Oct. 28, 2014

(86) PCT No.: PCT/US2014/062644
§ 371 (c)(1),
(2) Date: Apr. 11, 2016

(87) PCT Pub. No.: WO2015/066019
PCT Pub. Date: May 7, 2015

(65) Prior Publication Data
US 2016/0256417 A1 Sep. 8, 2016

Related U.S. Application Data

(60) Provisional application No. 61/896,173, filed on Oct. 28, 2013.

(51) Int. Cl.
*A61K 31/137* (2006.01)
*A61K 31/4045* (2006.01)
(Continued)

(52) U.S. Cl.
CPC ........ *A61K 31/137* (2013.01); *A61K 31/4045* (2013.01); *A61K 31/4184* (2013.01); *A61K 31/519* (2013.01); *A61K 45/06* (2013.01)

(58) Field of Classification Search
None
See application file for complete search history.

(56) References Cited

U.S. PATENT DOCUMENTS 2,407,167 A 9/1946 Kulz
5,352,688 A 10/1994 Kaminski
(Continued)

FOREIGN PATENT DOCUMENTS

DE 102011015842 A1 11/2012
EP 1138666 B1 3/2004
(Continued)

OTHER PUBLICATIONS

PCT International Search Report and Written Opinion for PCT International Application No. PCT/US2014/062644 dated Jan. 6, 2015.
(Continued)

*Primary Examiner* — Karl J Puttlitz
(74) *Attorney, Agent, or Firm* — Saul Ewing Arnstein & Lehr LLP; Kathryn Doyle; Domingos J. Silva

(57) ABSTRACT

The present invention provides a method of treating or preventing an attention and/or cognitive disorder in a subject in need thereof, comprising administering to the subject a compound useful within the invention. The present invention further provides a method of treating or preventing dementia associated with a neurodegenerative disorder in a (Continued)

subject in need thereof, comprising administering to the subject a compound useful within the invention.

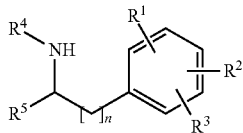

(I)

13 Claims, 11 Drawing Sheets

(51) Int. Cl.
A61K 31/4184 (2006.01)
A61K 45/06 (2006.01)
A61K 31/519 (2006.01)

(56) References Cited

U.S. PATENT DOCUMENTS

| 6,031,003 | A | 2/2000 | Nemeth et al. |
| 7,825,109 | B2 | 11/2010 | Nakade et al. |
| 2008/0058356 | A1 | 3/2008 | Crespo Crespo et al. |
| 2009/0281149 | A1 | 11/2009 | Scott et al. |
| 2010/0143322 | A1 | 6/2010 | Wolf et al. |
| 2011/0117214 | A1 | 5/2011 | Newbold et al. |

FOREIGN PATENT DOCUMENTS

| WO | 9323035 | A2 | 11/1993 |
| WO | 9943678 | A1 | 9/1999 |
| WO | 2004113391 | A2 | 12/2004 |
| WO | 2006078239 | A1 | 7/2006 |
| WO | 2006083692 | A2 | 8/2006 |
| WO | 2006085149 | A2 | 8/2006 |
| WO | 2006097744 | A2 | 9/2006 |
| WO | 2007002516 | A2 | 1/2007 |
| WO | 2007022415 | A2 | 2/2007 |
| WO | 2007133772 | A2 | 11/2007 |
| WO | 2008052953 | A1 | 5/2008 |
| WO | 2008107335 | A1 | 9/2008 |
| WO | 2008113364 | A2 | 9/2008 |
| WO | 2009136175 | A1 | 11/2009 |
| WO | 2009140204 | A2 | 11/2009 |
| WO | 2010118055 | * | 10/2010 |
| WO | 2012021629 | A2 | 2/2012 |
| WO | 2013029060 | * | 2/2013 |

OTHER PUBLICATIONS

CAS RN 1183990-06-8; Benzenepropanamine, 2-chloro-N,α-dimethyl- (CA Index Name), STN Entry Date Sep. 14, 2009.
CAS RN 855397-31-8; Phenol, 2-(3-aminobutyl)- (CA Index Name), STN Entry Date Jul. 15, 2005.
CAS RN 51062-15-8; Benzenepropanamine, 4-methoxy-α-methyl- (CA Index Name), STN Entry Date Nov. 16, 1984.
CAS RN 1099621-82-5; Benzenepropanamine, 2-bromo-α-methyl- (CA Index Name), STN Entry Date Feb. 2, 2009.
CAS RN 943109-70-4; Benzenepropanamine, 2-methoxy-α-methyl- (CA Index Name), STN Entry Date Jul. 22, 2007.

CAS RN 878684-94-7; Benzenepropanamine, 3,4-diethoxy- (CA Index Name), STN Entry Date Mar. 31, 2006.
CAS RN 1092924-49-6; Benzenepropanamine, 2-fluoro-a-methyl- (CA Index Name), STN Entry Date Jan. 7, 2005.
"PubChemSubstance Direct Submission SID 84973441, 2-[(2-chlorobenzyl)amino]butan-1-01-6 Substance Summary", <http://pubchem.ncbi.nlm.nih.gov/summary/summary.cgi?sid=84973441>, Jul. 22, 2009, [Retrieved from the Internet Mar. 28, 2013].
Ask, et al., "Selective inhibition of monoamine oxidase by p-aminosubstituted phenylalkylamines in catecholaminergic neurones", Neuropharmacology.25(1), Jan. 1986, 33-40.
Berridge, et al., "Differential sensitivity to psychostimulants across prefrontal cognitive tasks: differential involvement of noradrenergic $\alpha_1$ - and $\alpha_2$-receptors", Biol Psychiatry. 71(5), Mar. 1, 2012, 467-473.
Boeckler, et al., "CoMFA and CoMSIA investigations revealing novel insights into the binding modes of dopamine D3 receptor agonists", J Med Chem. 48(7), Apr. 7, 2005, 2493-2508.
Clarke, et al., "Cabergoline versus bromocriptine for levodopa-induced complications in Parkinson's disease", Cochrane Database Syst Rev. (1), 2001, CD001519.
Costall, et al., "Dyskinetic phenomena caused by the intrastriatal injection of phenylethylamine, phenylpiperazine, tetrahydroisoquinoline and tetrahydronaphthalene derivatives in the guinea pig", Eur J Pharmacol. 31(1), Mar. 1975, 94-109.
Dukat, et al., "Structure-activity relationships for the binding of arylpiperazines and arylbiguanides at 5-HT3 serotonin receptors", J Med Chem. 39(20), Sep. 27, 1996, 4017-4026.
Grundt, et al., "Heterocyclic analogues of N-(4-(4-(2,3-dichlorophenyl)piperazin-1-yl)butyl)arylcarboxamides with functionalized linking chains as novel dopamine D3 receptor ligands: potential substance abuse therapeutic agents", J Med Chem. 50(17), Aug. 23, 2007, 4135-4146.
Klein, et al., "Synthesis of chiral 1,4-disubstituted-1,2,3-triazole derivatives from amino acids", Molecules. 14(12), Dec. 9, 2009, 5124-5143.
Kuzhikandathil, et al., "Identification and characterization of a novel class of atypical dopamine receptor agonists", Pharm Res. 29(8), Aug. 2012, 2264-2275.
Muglia, et al., "A transmission disequilibrium test of the Ser9/Gly dopamine D3 receptor gene polymorphism in adult attention-deficit hyperactivity disorder", Behav Brain Res. 130(1-2), Mar. 10, 2002, 91-95.
Newman, et al., "N-(4-(4-(2,3-dichloro- or 2-methoxyphenyl)piperazin-1-yl)butyl)heterobiarylcarboxamides with functionalized linking chains as high affinity and enantioselective D3 receptor antagonists", J Med Chem. 52(8), Apr. 23, 2009, 2559-2570.
Stefani, et al., "Glutamate receptors in the rat medial prefrontal cortex regulate set-shifting ability", Behav Neurosci. 117(4), Aug. 2003, 728-737 (Abstract Only).
Wang, et al., "Suppression of Levodopa-Induced Dyskinesia in Parkinson's Disease", Chinese Journal of Clinical Neurosciences 9(2), 2001, 215-216 (Abstract Only).
Westrich, et al., "Development of tolerance in D3 dopamine receptor signaling is accompanied by distinct changes in receptor conformation", Biochem Pharmacol. 79(6), Mar. 15, 2010, 897-907.
Yraola, et al., "New efficient substrates for semicarbazide-sensitive amine oxidase/VAP-1 enzyme: analysis by SARs and computational docking", J Med Chem. 49(21), Oct. 19, 2006, 6197-6208.
European Search Report for European Patent Application No. 14858402.2 dated Jul. 17, 2017.
Nakajima, et al., "The potential role of dopamine $D_3$ receptor neurotransmission in cognition", Eur Neuropsychopharmacol. 23(8), 2013, 799-813.

* cited by examiner

TREATMENTS FOR ATTENTION AND COGNITIVE DISORDERS, AND FOR DEMENTIA ASSOCIATED WITH A NEURODEGENERATIVE DISORDER

CROSS-REFERENCE TO RELATED APPLICATIONS

The present application is a 35 U.S.C. §371 national phase application from, and claims priority to, International Application No. PCT/US2014/062644, filed Oct. 28, 2014, and published under PCT Article 21(2) in English, which claims priority under 35 U.S.C. §119(e) to U.S. Provisional Application No. 61/896,173, filed Oct. 28, 2013, all of which applications are incorporated herein by reference in their entireties.

BACKGROUND OF THE INVENTION

The family of G-protein coupled receptors (GPCRs) is one of the most important classes of proteins from both functional and structural standpoints. The human genome contains nearly 950 genes coding for GPCRs, of which nearly 450 genes have been implicated as therapeutic targets. Ligand binding to GPCRs induces multiple receptor conformations and different ligands may stabilize distinct receptor conformations (Kenakin & Miller, 2010, Pharmacol. Rev. 62(2):265-304). The concept of functional selectivity is based on the hypothesis that distinct receptor conformations recruit distinct signaling proteins, leading to preferential activation of one signaling pathway over another (Mailman, 2007, Trends Pharmacol. Sci. 28(8):390-396). In addition to selecting the signaling pathways, agonist-induced receptor conformations can also potentially affect receptor signaling properties.

Among the GPCRs, the subfamily of dopamine receptors has attracted attention from biologists and pharmacologists. In the central nervous system, dopamine receptors are widely expressed and involved in the control of locomotion, cognition, emotion and neuroendocrine secretion. In the peripheral system, dopamine receptors are present more prominently in kidney, vasculature and pituitary, where they affect mainly sodium homeostasis, vascular tone, and hormone secretion. While there are numerous examples of functionally-selective ligands that activates one signaling cascade preferentially over others, functionally-selective ligands that alter receptor signaling properties are rare and have not been described for dopamine receptors.

The neurotransmitter dopamine controls a wide variety of physiological and behavioral functions in mammals via five major subtypes of dopamine receptors. They are broadly classified into the "$D_1$-like" and "$D_2$-like" dopamine receptors based on pharmacology and function. The $D_1$-like receptors consist of $D_1$ and $D_5$ receptors, while the $D_2$-like receptors consist of $D_2$, $D_3$ and $D_4$ receptors.

The $D_3$ receptor primarily couples to the pertussis toxin-sensitive $G_\alpha$-proteins ($G_i/G_o$) (Ahlgren-Beckendorf & Levant, 2004, J. Recept. Signal Transduct. Res. 24(3):117-130). When transfected into different cell lines, the $D_3$ receptor couples to adenylyl cyclase V isoform (Robinson & Caron, 1997, Mol. Pharmacol. 52:508-514) and initiates signaling events including phosphorylation of mitogen-activated protein (MAP) kinases (Cussac et al., 1999, Mol. Pharmacol. 56(5):1025-103). $D_2$ and $D_3$ dopamine receptors also modulate potassium and calcium channel function (Seabrook et al., 1994, Br. J. Pharmacol. 111:391-393; Werner et al., 1996, Mol. Pharmacol. 49:656-661). Transfected $D_3$ receptors couple robustly to natively expressed G-protein coupled inward rectifier potassium (GIRK) and voltage-gated P/Q type calcium channels, and inhibit firing of spontaneous action potentials and secretory activity in the AtT-20 neuroendocrine cell line (Kuzhikandathil & Oxford, 1999, J. Neurosci. 19(5):1698-1707; Kuzhikandathil & Oxford, 2000, J. Gen. Physiol. 115:697-706; Kuzhikandathil et al., 1998, Mol. Cell Neurosci. 12:390-402). The $D_3$ receptor further couples to natively expressed adenylyl cyclase V (Kuzhikandathil & Bartoszyk, 2006, Neuropharm. 51:873-884), MAP kinases (Westrich & Kuzhikandathil, 2007, Biochim. Biophys. Acta-MCR 1773:1747-1758) and ion channels (Kuzhikandathil & Oxford, 1999, J. Neurosci. 19(5):1698-1707; Kuzhikandathil & Oxford, 2000, J. Gen. Physiol. 115:697-706; Kuzhikandathil et al., 1998, Mol. Cell Neurosci. 12:390-402; Kuzhikandathil et al., 2004, Mol. Cell Neurosci. 26:144-155) in AtT-20 cells.

Dopamine receptors are targets for the treatment of various neurological and psychiatric disorders, such as Parkinson's Disease, schizophrenia, drug addiction, depression, bipolar disorder, attention deficit hyperactivity syndrome, Tourette's Syndrome, Huntington's Disease and migraine.

Norepinephrine, also known as noradrenaline or 4-[(1R)-2-amino-1-hydroxy ethyl]benzene-1,2-diol, is a catecholamine that acts as a hormone and a neurotransmitter. Norepinephrine is the hormone and neurotransmitter most responsible for concentration, in contrast to the chemically similar hormone dopamine, also known as 4-(2-aminoethyl) benzene-1,2-diol), which is most responsible for alertness. Areas of the body that produce or are affected by norepinephrine are described as noradrenergic.

Norepinephrine has an important role as the neurotransmitter released from the sympathetic neurons to increase the rate of contractions in the heart. As a stress hormone, norepinephrine affects parts of the brain, such as the amygdala, where attention and responses are controlled. Along with epinephrine (also known as adrenaline or (R)-4-(1-Hydroxy-2-(methylamino)ethyl)benzene-1,2-diol), norepinephrine underlies the fight-or-flight response, directly increasing heart rate, triggering the release of glucose from energy stores, and increasing blood flow to skeletal muscle. It increases the brain's oxygen supply, and may also suppress neuro-inflammation when released diffusely in the brain from the locus coeruleus. As a drug, norepinephrine increases blood pressure by increasing vascular tone (tension of vascular smooth muscle) through α-adrenergic receptor activation.

Norepinephrine has potentially beneficial effects on attention deficit/hyperactivity disorder, depression and hypotension, but, as with other catecholamines, it cannot be used in the clinic because it does not cross the blood-brain barrier. However, drugs that inhibit norepinephrine transporter in the prefrontal cortex (PFC), such as methylphenidate (MPH, also known as methyl phenyl(piperidin-2-yl)acetate), increase extracellular concentrations of norepinephrine in brain tissue and increase rodent performance in a sustained attention task.

Non-norepinephrine drugs such as amphetamines are used to stimulate brain activity levels. For people with attention-deficit/hyperactivity disorder (ADHD), psychostimulant medications such as amphetamines (ADDERALL® or DESOXYN®) are prescribed to increase both levels of norepinephrine and dopamine. Methylphenidate (RITALIN® or CONCERTA®, a dopamine reuptake inhibitor) and atomoxetine (STRATTERA® or (3R)—N-methyl-3-(2-methylphenoxy)-3-phenylpropan-1-amine; a selective norepinephrine reuptake inhibitor) increase both norepinephrine and dopamine in the prefrontal cortex equally, but only dopamine (in the case of methylphenidate) and norepinephrine (in the case of atomoxetine) elsewhere in other parts of the brain. Other serotonin-norepinephrine reuptake inhibitors (SNRIs) currently approved as antidepressants are also used off-label for treatment of ADHD. The few medications available to treat ADHD, such as MPH, have been illegally used by students and teenagers as a stimulant to boost their grades.

In addition to its neurotransmitter role, the norepinephrine from locus coeruleus cells locally diffuses from "varicosities," providing an endogenous anti-inflammatory agent in the microenvironment around the neurons, glial cells, and blood vessels in the neocortex and hippocampus. Up to 70% of norepinephrine projecting cells are lost in Alzheimer's Disease. Norepinephrine stimulates mouse microglia to suppress Aβ-induced production of cytokines and their phagocytosis of Aβ, suggesting this loss might have a role in causing this disease. There are currently no medications that may be used to treat dementia associated with a neurodegenerative disorder such as Parkinson's Disease and Alzheimer's Disease.

There is a need in the art for novel methods of treating or preventing an attention disorder and/or cognitive disorder in a subject in need thereof. Further, there is a need in the art for novel methods of treating or preventing dementia associated with a neurodegenerative disorder in a subject in need thereof. The present invention fulfills these needs.

BRIEF SUMMARY OF THE INVENTION

The invention includes a method of treating or preventing an attention disorder or a cognitive disorder in a subject in need thereof. The invention further includes a method of treating or preventing dementia associated with a neurodegenerative disease in a subject in need thereof.

In certain embodiments, the method comprises administering to the subject a therapeutically effective amount of at least one compound selected from the group consisting of:
a compound of formula (I):

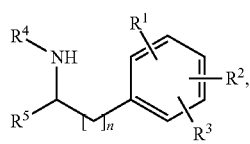

wherein in (I):

$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, n is 2, 3, 4 or 5;

a compound of formula (II):

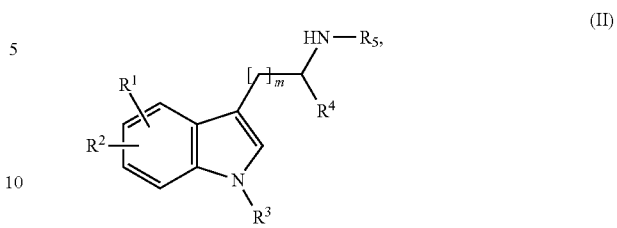

wherein in (II):

$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^3$ and $R^4$ are independently selected from the group consisting of H, $C_{1-6}$ alkyl, and substituted $C_{1-6}$ alkyl;

$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, m is 1, 2, or 3;

2,7-diamino-5-(4-fluorophenyl)-4-oxo-3,4,5,6-tetrahydropyrido[2,3-d]pyrimidine-6-carbonitrile;
(Z)-2-(1H-benzo[d]imidazol-2-yl)-N'-hydroxy-3-(4-methoxyphenyl)propanimidamide;
a pharmaceutically acceptable salt or solvate thereof, and any mixtures thereof.

In certain embodiments, the attention or cognitive disorder comprises ADD or ADHD. In other embodiments, administration of the compound improves cognitive flexibility in the subject. In yet other embodiments, administration of the compound improves sustained attention in the subject.

In certain embodiments, the neurodegenerative disease comprises at least one selected from the group consisting of Alzheimer's Disease, Parkinson's Disease, Huntington's Disease, transmissible spongiform encephalopathies, chronic traumatic encephalopathy (CTE) resulting from repeated traumatic brain injuries, and amyotrophic lateral sclerosis.

In certain embodiments, in formula (I) $R^1$, $R^2$ and $R^3$ are independently selected from the group consisting of H, cyano, halo, alkoxy, nitro, $C_{1-6}$ alkyl, and carboxy. In other embodiments, in formula (I) $R^4$ and $R^5$ are independently selected from the group consisting of H, $C_{1-6}$ alkyl, and substituted $C_{1-6}$ alkyl. In yet other embodiments, in formula (I) n is 2. In yet other embodiments, in formula (II) m is 1.

In certain embodiments, the at least one compound is selected from the group consisting of: 2-amino-4-(2-chlorophenyl)butan-1-ol; 2-(3-aminohexyl)phenol; 4-(2-chlorophenyl)-2-methylamino-butane; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4- methoxyphenyl)propanimidamide; a pharmaceutically acceptable salt or solvate, and mixtures thereof.

In certain embodiments, the composition further comprises at least one drug selected from the group consisting of methylphenidate, dextroamphetamine, dextroamphetamine-amphetamine, lisdexamfetamine, ADHD medication, antidepressants, clonidine, guanfacine, and a salt or solvate thereof.

In certain embodiments, the subject is a mammal. In other embodiments, the subject is human.

BRIEF DESCRIPTION OF THE DRAWINGS

For the purpose of illustrating the invention, there are depicted in the drawings certain embodiments of the present invention. However, the invention is not limited to the precise arrangements and instrumentalities of the embodiments depicted in the drawings.

FIG. 10, comprising FIG. 10A illustrates number of trials to reach the criterion, and FIG. 10B illustrates overall performance upon administration of saline or SK609.

DETAILED DESCRIPTION OF THE INVENTION

Figure 1:
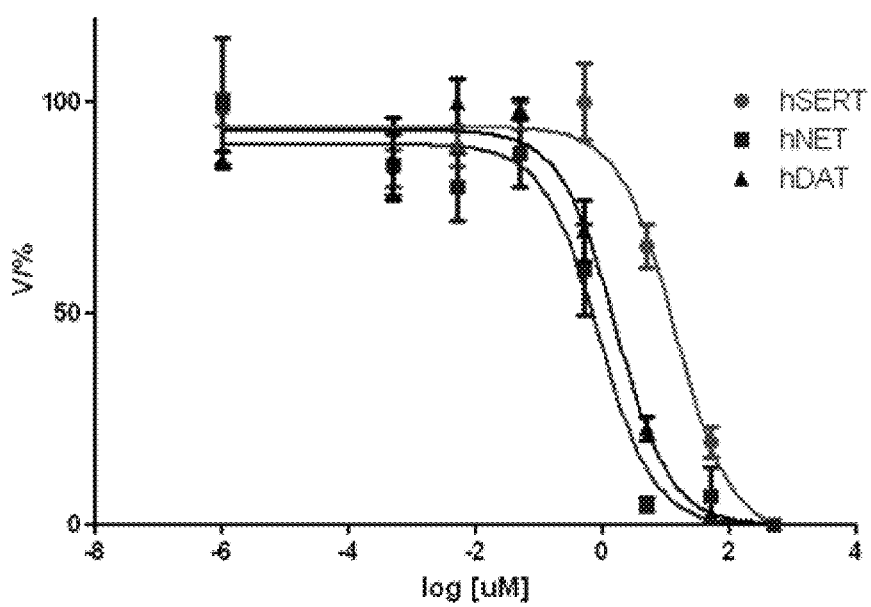
FIG. 1 is a graph illustrating the effect of SK609 (also known as 4-(2-chlorophenyl)-butan-2-amine or a salt thereof) on the efflux of the various monoamine neurotransmitters measured as a percentage of the vehicle. The $IC_{50}$ value for hSERT was 35.85 µM, for hDAT was 8.5 µM, and for hNET was 290 nM.
Figure 2:
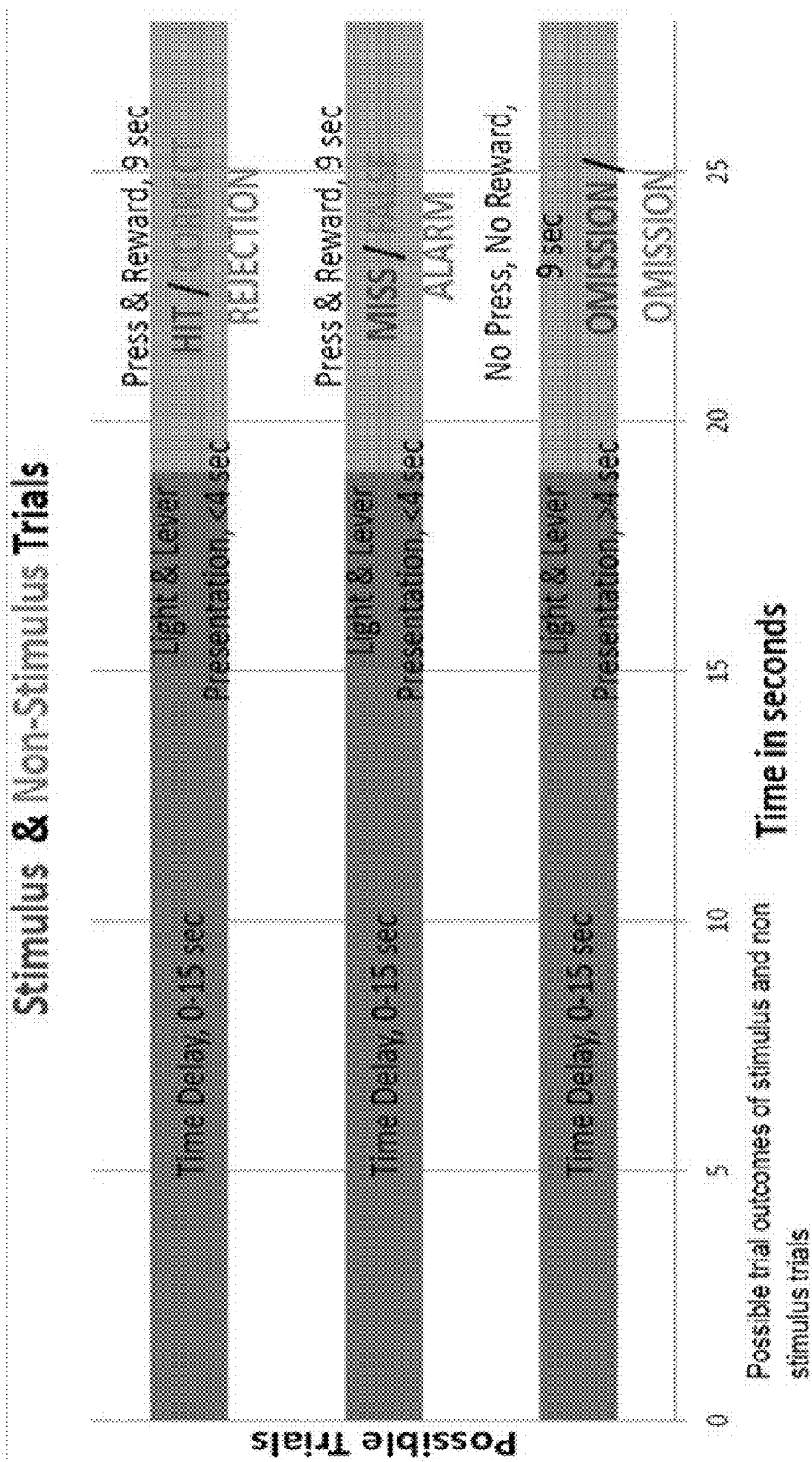
FIG. 2 is a schematic illustration of the experimental set-up sustained attention task animal study described herein.
Figure 3:
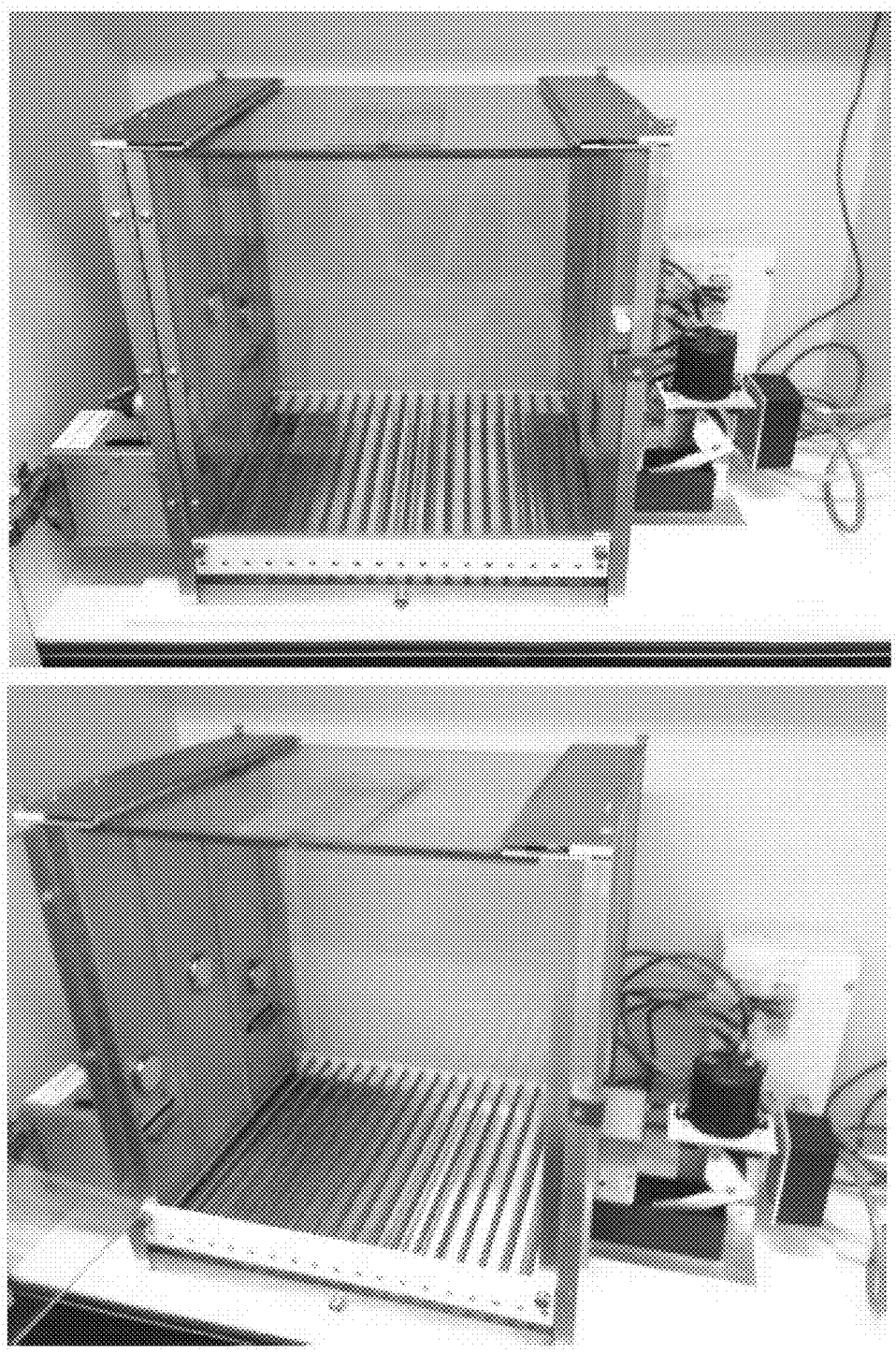
FIG. 3 is a set of pictures illustrating the sustained attention task apparatus described herein. Operant conditioning chambers pictured with presentation lights, levers and water reward mechanism. The operant chambers are contained in an air-circulated and sound-isolated cabinet.

The present invention relates to the unexpected identification of compounds that are useful to treat or prevent an attention and/or cognitive disorder, such as but not limited to attention deficit disorder (ADD) or attention deficit hyperactivity disorder (ADHD). The present invention further relates to the unexpected identification of compounds that are useful to treat or prevent dementia associated with a neurodegenerative disorder.

In certain embodiments, the neurodegenerative disorder comprises at least one selected from the group consisting of Alzheimer's Disease (AD), Parkinson's Disease (PD), Huntington's Disease (HD), transmissible spongiform encephalopathies (TSEs), and amyotrophic lateral sclerosis (ALS).

In certain embodiments, the compound useful within the invention is a selective $D_3$ receptor agonist and a selective norepinephrine transporter (NET) inhibitor. In other embodiments, the compounds useful within the invention are not selective activators of the dopamine transporter or serotonin transporter. In yet other embodiments, the compounds useful within the invention are not selective inhibitors of the dopamine transporter or serotonin transporter. Without wishing to be limited by any theory, a compound that is a selective $D_3$ receptor agonist and a selective norepinephrine transporter inhibitor blocks NET, increases extracellular norepinephrine, and improves performance in a sustained attention task.

In certain embodiments, the compounds of the present invention improve cognitive flexibility in a subject. In other embodiments, the compounds of the present invention improve sustained attention in a subject. In yet other embodiments, the compounds of the present invention improve cognitive flexibility and sustained attention in a subject. Without wishing to be limited by any theory, these improvement are mediated specifically through the targets dopamine $D_3$ receptor and NET. In certain embodiments, the improvement in sustained attention can be blocked by the use of a $D_3$ receptor antagonist and α1 adrenergic receptor antagonist, suggesting the target engagement by the compounds of present invention.

As demonstrated herein, SK609, an atypical selective agonist of the $D_3$ receptor, was characterized against a panel of monoamine neurotransmitter transporters and other G-protein coupled receptors, and these studies revealed novel polypharmacological effects that contribute significantly to its atypical profile. In addition to its highly selective $D_3$ agonist activity, SK609 exhibited selective NET antagonism. Further, SK609 had no effect on dopamine transporters (DAT) or serotonin transporters (SERT), and likely does not produce the stimulant effects as seen with amphetamine compounds.

The results described herein demonstrate that SK609 increased male Sprague-Dawley rat performance in the sustained attention task in a dose dependent manner with a peak effect at 8 mg/kg. SK609-induced changes in performance followed an inverted-U curve, which is the same dose-response relationship noted previously for MPH. In addition, pre-treatment with the α1-adrenergic receptor antagonist prazosin reversed the attention-enhancing effects of SK609 and MPH completely, while the dopamine $D_2$-like receptor antagonist raclopride had complete inhibition, suggesting a role for norepinephrine and dopaminergic modulation in the action of these compounds and PFC-related cognitive tasks.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in animal physiology, pharmacology, organic chemistry, and peptide chemistry are those well known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used.

As used herein, the term "atomoxetine" refers to (3R)—N-methyl-3-(2-methylphenoxy)-3-phenylpropan-1-amine, or a salt or solvate thereof.

The term "container" includes any receptacle for holding the pharmaceutical composition. For example, In certain embodiments, the container is the packaging that contains the pharmaceutical composition. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

As used herein, the term "DAT" refers to dopamine transporter.

As used herein, the term "L-DOPA" refers to levodopa, also known as L-3,4-dihydroxyphenylalanine, or a salt or solvate thereof.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "ES609" or "ES0609" refers to 4-(2-chlorophenyl)-butan-2-amine, or a salt or solvate thereof.

"Instructional material" as that term is used herein includes a publication, a recording, a diagram, or any other medium of expression that may be used to communicate the usefulness of the compounds of the present invention. In some instances, the instructional material may be part of a kit useful for effecting alleviating or treating the various diseases or disorders recited herein. Optionally, or alternately, the instructional material may describe one or more methods of alleviating the diseases or disorders in a cell or a tissue of a mammal. The instructional material of the kit may, for example, be affixed to a container that contains the compounds of the present invention or be shipped together with a container that contains the compounds. Alternatively, the instructional material may be shipped separately from the container with the intention that the recipient uses the instructional material and the compound cooperatively. For example, the instructional material is for use of a kit; instructions for use of the compound; or instructions for use of a formulation of the compound.

As used herein, the term "MPH" refers to methylphenidate or methyl phenyl(piperidin-2-yl)acetate, or a salt or solvate thereof.

As used herein, the term "NET" refers to norepinephrine transporter.

As used herein, the term "patient," "individual" or "subject" refers to a human or a non-human mammal. Non-human mammals include, for example, livestock and pets, such as ovine, bovine, porcine, canine, feline and murine mammals. In certain embodiments, the patient, individual or subject is human.

As used herein, the term "PFC" refers to prefrontal cortex.

As used herein, the term "polypeptide" refers to a polymer composed of amino acid residues, related naturally occurring structural variants, and synthetic non-naturally occurring analogs thereof linked via peptide bonds. Synthetic polypeptides may be synthesized, for example, using an automated polypeptide synthesizer. As used herein, the term "protein" typically refers to large polypeptides. As used herein, the term "peptide" typically refers to short polypeptides. Conventional notation is used herein to represent polypeptide sequences: the left-hand end of a polypeptide sequence is the amino-terminus, and the right-hand end of a polypeptide sequence is the carboxyl-terminus.

As used herein, amino acids are represented by the full name thereof, by the three letter code corresponding thereto, or by the one-letter code corresponding thereto, as indicated below: Aspartic Acid, Asp, D; Glutamic Acid, Glu, E; Lysine, Lys, K; Arginine, Arg, R; Histidine, His, H; Tyrosine, Tyr, Y; Cysteine, Cys, C; Asparagine, Asn, N; Glutamine, Gln, Q; Serine, Ser, S; Threonine, Thr, T; Glycine, Gly, G; Alanine, Ala, A; Valine, Val, V; Leucine, Leu, L; Isoleucine, Ile, I; Methionine, Met, M; Proline, Pro, P; Phenylalanine, Phe, F; Tryptophan, Trp, W.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the phrase "pharmaceutically acceptable salt" refers to a salt of the administered compounds prepared from pharmaceutically acceptable non-toxic acids, including inorganic acids, organic acids, solvates, hydrates, or clathrates thereof. Pharmaceutically unacceptable salts may nonetheless possess properties such as high crystallinity, which have utility in the practice of the present invention, such as for example utility in process of synthesis, purification or formulation of compounds useful within the methods of the present invention. Salts may be comprised of a fraction of one, one or more than one molar equivalent of acid or base with respect to any compound of the present invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxy benzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluene sulfonic, sulfanilic, cyclohexylaminosulfonic, stearic, alginic, β-hydroxybutyric, salicylic, galactaric, galacturonic acid, glycerophosphonic acids and saccharin (e.g., saccharinate, saccharate).

Suitable pharmaceutically acceptable base addition salts of compounds of the present invention include, for example, ammonium salts, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methyl glucamine) and procaine. All of these salts may be prepared from the corresponding compound by reacting, for example, the appropriate acid or base with the compound.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the present invention are known in the art and described, for example in Remington's Pharmaceutical Sciences (Genaro, Ed., Mack Publishing Co., 1985, Easton, Pa.), which is incorporated herein by reference.

As used herein, the term "prazosin" refers to 2-[4-(2-furoyl)piperazin-1-yl]-6,7-dimethoxyquinazolin-4-amine, or a salt or solvate thereof.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "raclopride" refers to 3,5-dichloro-N-{[(2S)-1-ethylpyrrolidin-2-yl]methyl}-2-hydroxy-6-methoxybenzamide, or a salt or solvate thereof.

As used herein, the term "SERT" refers to serotonin transporter.

As used herein, the term "SRT property" or "slow response termination" as applying to the $D_3$ receptor refers to the increase in time taken to terminate the signaling function of the $D_3$ receptor, after removal of the agonist.

As used herein, the term "tolerance property" as applying to the $D_3$ receptor refers to the progressive decrease in receptor signaling function upon repeated stimulation by classical agonists, including dopamine.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

As used herein, the term "VI" refers to vigilante index.

Throughout this disclosure, various aspects of the present invention can be presented in a range format. It should be understood that the description in range format is merely for convenience and brevity and should not be construed as an inflexible limitation on the scope of the present invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.1, 5.3, 5.5, and 6. This applies regardless of the breadth of the range.

Compounds

The compounds useful within the invention may be synthesized using techniques well-known in the art of organic synthesis.

In one aspect, the compounds useful within the invention are selective $D_3$ receptor agonists and selective norepinephrine transporter (NET) antagonists. In another aspect, the compounds useful within the invention are not agonists of the dopamine transporter or serotonin transporter. In yet another aspect, the compounds useful within the invention are not an antagonist of the dopamine transporter or serotonin transporter.

In another aspect, the compound useful within the present invention has the formula (I):

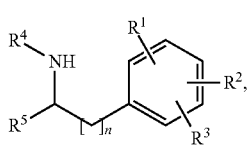

(I)

wherein in (I):

$R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, substituted aryl-($C_{1-3}$)alkyl, carboxy, alkylcarboxy, formyl, alkyl-carbonyl, aryl-carbonyl, and heteroaryl-carbonyl;

$R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, substituted aryl, aryl-($C_{1-3}$)alkyl, and substituted aryl-($C_{1-3}$)alkyl; and, n is 2, 3, 4 or 5; or a pharmaceutically acceptable salt or solvate thereof.

In certain embodiments, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, carboxy, alkylcarboxy, formyl, alkyl-carbonyl, aryl-carbonyl, and heteroaryl-carbonyl. In other embodiments, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, carboxy, alkylcarboxy, formyl, and alkyl-carbonyl. In yet other embodiments, $R^1$, $R^2$ and $R^3$ are independently selected from the group consisting of H, cyano, hydroxyl, amino, acetamido, halo, alkoxy, nitro, $C_{1-6}$ alkyl, substituted $C_{1-6}$ alkyl, heteroalkyl, and carboxy. In yet other embodiments, $R^1$, $R^2$ and $R^3$ are independently selected from the group consisting of H, cyano, hydroxyl, amino, acetamido, halo, alkoxy, nitro, $C_{1-6}$ alkyl, and carboxy. In yet other embodiments, $R^1$, $R^2$ and $R^3$ are independently selected from the group consisting of H, cyano, halo, alkoxy, nitro, $C_{1-6}$ alkyl, and carboxy. In yet other embodiments, $R^1$ and $R^2$ are H, and $R^3$ is chloro. In yet other embodiments, $R^1$, $R^2$ and $R^3$ are either independently or in combination selected from the group consisting of H, fluoro, chloro, bromo, iodo, methoxy, ethoxy, hydroxyl, methyl, ethyl or other lower alkyl or aryl groups.

In certain embodiments, n is 2, 3 or 4. In other embodiments, n is 2 or 3. In yet other embodiments, n is 2.

In certain embodiments, $R^4$ and $R^5$ are independently selected from the group consisting of H, $C_{1-6}$ alkyl, substituted $C_{1-6}$ alkyl, heteroalkyl, heterocyclyl, substituted heterocyclyl, aryl, and substituted aryl. In other embodiments, $R^4$ and $R^5$ are independently selected from the group consisting of H, $C_{1-6}$ alkyl, substituted $C_{1-6}$ alkyl, heteroalkyl, heterocyclyl, and substituted heterocyclyl. In yet other embodiments, $R^4$ and $R^5$ are independently selected from the group consisting of H, $C_{1-6}$ alkyl, substituted $C_{1-6}$ alkyl, and heteroalkyl. In yet other embodiments, $R^4$ and $R^5$ are independently selected from the group consisting of H, $C_{1-6}$ alkyl, and substituted $C_{1-6}$ alkyl. In yet other embodiments, $R^4$ and $R^5$ are methyl. In yet other embodiments, $R^5$ is H, methyl, ethyl, prop-1-yl, prop-2-yl, hydroxymethyl, 1-hydroxy-ethyl, 2-hydroxy-ethyl, 1-hydroxy-prop-1-yl, 2-hydroxy-prop-1-yl, 3-hydroxy-prop-1-yl, 1-hydroxy-prop-2-yl or 2-hydroxy-prop-2-yl.

In certain embodiments, the compound useful within the invention is selected from the group consisting of:

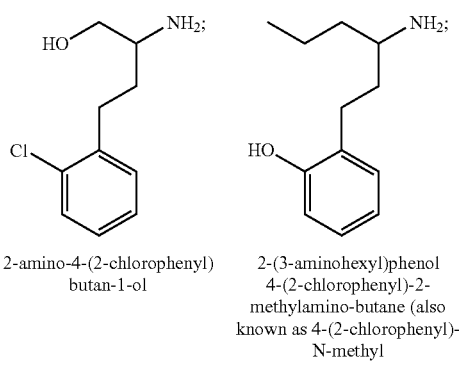

2-amino-4-(2-chlorophenyl) butan-1-ol 2-(3-aminohexyl)phenol 4-(2-chlorophenyl)-2-methylamino-butane (also known as 4-(2-chlorophenyl)-N-methyl

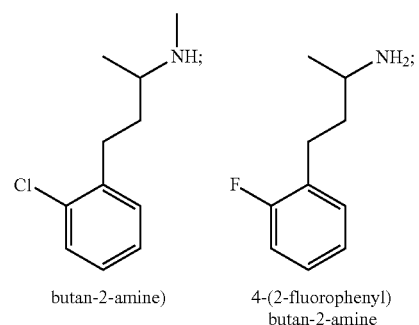

butan-2-amine)

4-(2-fluorophenyl) butan-2-amine

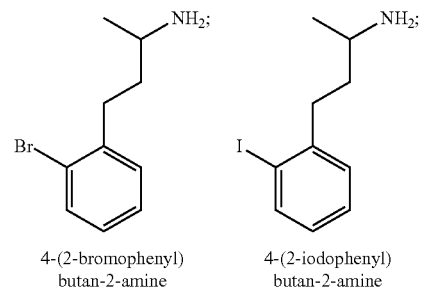

4-(2-bromophenyl) butan-2-amine 4-(2-iodophenyl) butan-2-amine

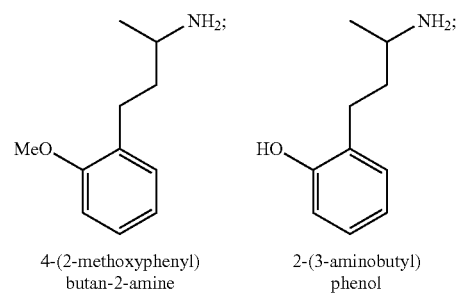

4-(2-methoxyphenyl) butan-2-amine 2-(3-aminobutyl) phenol

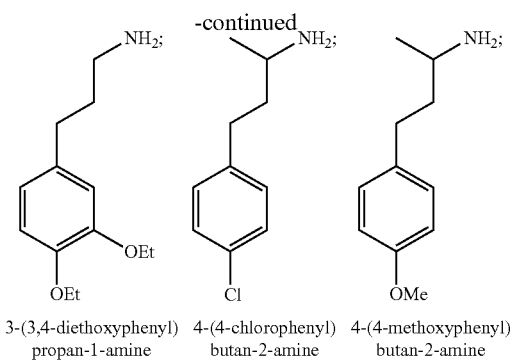

3-(3,4-diethoxyphenyl) propan-1-amine 4-(4-chlorophenyl) butan-2-amine 4-(4-methoxyphenyl) butan-2-amine mixtures thereof, or a pharmaceutically acceptable salt or solvate thereof.

In yet another aspect, the compound useful within the invention has the formula (II):

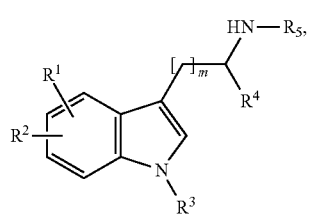

(II)

wherein in (II):

$R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, heteroalkyl, heterocyclyl, substituted heterocyclyl, aryl, substituted aryl, aryl-$(C_{1-3})$alkyl, substituted aryl-$(C_{1-3})$alkyl, carboxy, alkylcarboxy, formyl, alkyl-carbonyl, aryl-carbonyl, and heteroaryl-carbonyl;

$R^3$ and $R^4$ are independently selected from the group consisting of H, $C_{1-6}$ alkyl, and substituted $C_{1-6}$ alkyl or aryl or heteroaryl;

$R^5$ is selected from the group consisting of H, $C_{1-6}$ alkyl, substituted $C_{1-6}$ alkyl, heteroalkyl, heterocyclyl, substituted heterocyclyl, aryl, substituted aryl, aryl-$(C_{1-3})$alkyl, and substituted aryl-$(C_{1-3})$alkyl; and, m is 1, 2, or 3; or a pharmaceutically acceptable salt or solvate thereof.

In certain embodiments, $R^1$ and $R^2$ are independently selected from the group consisting of H, cyano, hydroxyl, amino, acetamido, halo, alkoxy, nitro, $C_{1-6}$ alkyl, substituted $C_{1-6}$ alkyl, carboxy, alkylcarboxy, formyl, alkyl-carbonyl, aryl-carbonyl, and heteroaryl-carbonyl. In other embodiments, $R^1$ and $R^2$ are independently selected from the group consisting of H, cyano, hydroxyl, halo, and alkoxy, $C_{1-6}$ alkyl, and substituted $C_{1-6}$ alkyl.

In certain embodiments, $R^3$ and $R^4$ are independently selected from the group consisting of H, and $C_{1-6}$ alkyl.

In certain embodiments, $R^5$ is selected from the group consisting of H, $C_{1-6}$ alkyl, and substituted $C_{1-6}$ alkyl.

In certain embodiments, m is 1, or 2.

In certain embodiments, the compound useful within the invention is selected from the group consisting of

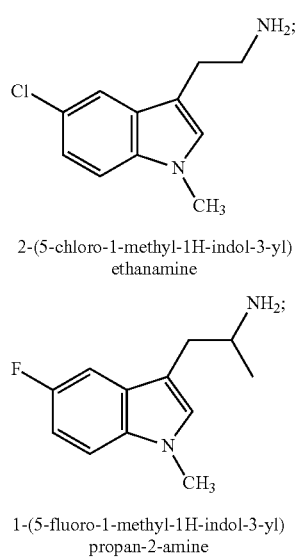

2-(5-chloro-1-methyl-1H-indol-3-yl) ethanamine 1-(5-fluoro-1-methyl-1H-indol-3-yl) propan-2-amine 1-(5-methoxy-1-methyl-1H-indol-3-yl)propan-2-amine mixtures thereof, or a pharmaceutically acceptable salt or solvate thereof.

In yet another aspect, the compound useful within the invention is selected from the group consisting of:

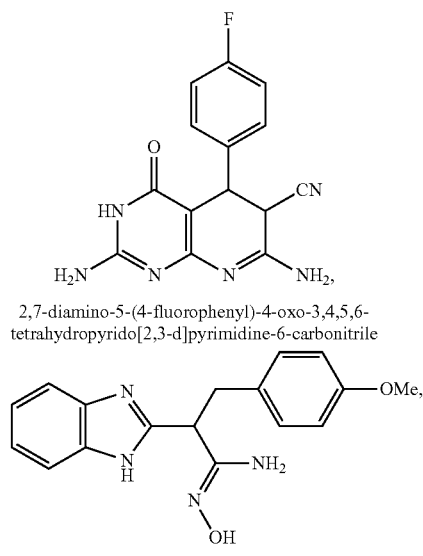

2,7-diamino-5-(4-fluorophenyl)-4-oxo-3,4,5,6-tetrahydropyrido[2,3-d]pyrimidine-6-carbonitrile (Z)-2-(1H-benzo[d]imidazol-2-yl)-N'-hydroxy-3-(4-methoxyphenyl)propanimidamide mixtures thereof, or a pharmaceutically acceptable salt or solvate thereof.

Methods

In one aspect, the invention includes a method of treating or preventing an attention disorder or cognitive disorder in a subject in need thereof. In certain embodiments, the attention disorder or cognitive disorder comprises ADD or ADHD.

In another aspect, the invention includes a method of treating or preventing dementia associated with a neurodegenerative disorder in a subject in need thereof. In certain embodiments, the neurodegenerative disorder comprises at least one selected from the group consisting of Alzheimer's Disease (AD), Parkinson's Disease (PD), Huntington's Disease (HD), transmissible spongiform encephalopathies (TSEs), chronic traumatic encephalopathy (CTE) resulting from repeated traumatic brain injuries, and amyotrophic lateral sclerosis (ALS).

In certain embodiments, the method comprises administering to the subject a pharmaceutical composition comprising a therapeutically effective amount of at least one compound of the present invention.

In certain embodiments, the compounds of the present invention improve cognitive flexibility in a subject. In other embodiments, the compounds of the present invention do not improve cognitive flexibility in a subject. In yet other embodiments, the compounds of the present invention improve sustained attention in a subject. In yet other embodiments, the compounds of the present invention do not improve sustained attention in a subject.

In certain embodiments, the compound useful within the invention is selected from the group consisting of: 2-amino-4-(2-chlorophenyl)butan-1-ol; 2-(3-aminohexyl) phenol; 4-(2-chlorophenyl)-2-methylamino-butane (also known as 4-(2-chlorophenyl)-N-methylbutan-2-amine); 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl) phenol; 3-(3,4-diethoxyphenyl)propan-1-amine; 4-(4-chlorophenyl)butan-2-amine; 4-(4-methoxyphenyl)butan-2-amine; 2-(5-chloro-1-methyl-1H-indol-3-yl)ethanamine; 1-(5-fluoro-1-methyl-1H-indol-3-yl)propan-2-amine; 1-(5-methoxy-1-methyl-1H-indol-3-yl)propan-2-amine; 2,7-diamino-5-(4-fluorophenyl)-4-oxo-3,4,5,6-tetrahydropyrido[2,3-d]pyrimidine-6-carbonitrile; (Z)-2-(1H-benzo[d]imidazol-2-yl)-N'-hydroxy-3-(4-methoxyphenyl) propanimidamide; mixtures thereof, or a pharmaceutically acceptable salt or solvate thereof. In certain embodiments, the subject is human.

Combination Therapies

The compounds of the present invention are intended to be useful in the methods of present invention in combination with one or more additional compounds useful for treating the diseases or disorders contemplated within the invention. These additional compounds may comprise compounds of the present invention or compounds, e.g., commercially available compounds, known to treat, prevent, or reduce the symptoms of the diseases or disorders contemplated within the invention.

In non-limiting examples, the compounds of the present invention may be used in combination with one or more of the following drugs: methylphenidate (CONCERTA®, METADATE®, and RITALIN®), dextroamphetamine (DEXEDRINE®), dextroamphetamine-amphetamine (ADDERALL XR®), lisdexamfetamine (VYVANSE®), ADHD medication such as atomoxetine (STRATTERA®), antidepressants such as bupropion (WELLBUTRIN®) and desipramine (NORPRAMIN®), clonidine (CATAPRES®), guanfacine (INTUNIV®, TENEX®), a salt or solvate thereof and mixtures thereof.

A synergistic effect may be calculated, for example, using suitable methods such as, for example, the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions useful within the present invention to a patient, preferably a mammal, more preferably a human, may be carried out using known procedures, at dosages and for periods of time effective to treat a disease or disorder in the patient. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the present invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the present invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the present invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions useful within the invention are formulated using one or more pharmaceutically acceptable excipients or carriers. In certain embodiments, the pharmaceutical compositions of the present invention comprise a therapeutically effective amount of at least one compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions useful within the invention are administered to the patient in dosages that range from one to five times per day or more. In other embodiments, the compositions useful within the invention are administered to the patient in range of dosages that include, but are not limited to, once every day, every two, days, every three days to once a week, and once every two weeks. It will be readily apparent to one skilled in the art that the frequency of administration of the various combination compositions useful within the invention will vary from individual to individual depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

Compounds for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 μg to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In some embodiments, the dose of a compound is from about 1 mg and about 2,500 mg. In some embodiments, a dose of a compound of the present invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., a drug used for treating a disease or disorder) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the present invention, alone or in combination with a second pharmaceutical agent; and instructions for using the compound to treat, prevent, or reduce one or more symptoms of a disease or disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the present invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically acceptable excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds may be in the form of tablets or capsules prepared by conventional means with pharmaceutically acceptable excipients such as binding agents (e.g., polyvinylpyrrolidone, hydroxypropylcellulose or hydroxypropyl methylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds of the present invention, and a further layer providing for the immediate release of a medication for treatment of a disease or disorder. Using a wax/pH-sensitive polymer mix, a gastric insoluble composition may be obtained in which the active ingredient is entrapped, ensuring its delayed release.

Parenteral Administration

For parenteral administration, the compounds may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the present invention may be administered in the form of microparticles, for example, by injection or in the form of wafers or discs by implantation.

In certain embodiments of the present invention, the compounds of the present invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound will depend on the age, sex and weight of the patient, the current medical condition of the patient and the progression of Parkinson's Disease in the patient being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

The compounds for use in the method of the present invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Example 1: Stimulus and Non-Stimulus Trials

The vigilance index (VI) of rats treated with SK609 was evaluated using the following protocol. Substantively, eight water restricted male Sprague-Dawley rats were trained in an operant task of sustained attention (McGaughy & Sarter, 1995, Psychopharm. 117:340-357). In response to both signal and non-signal conditions, a water reward was given for correct responses as a positive reinforcer. Rats were first trained by successive approximation to establish lever pressing behavior. Subjects were then trained to criterion performance on the sustained attention task with a 1,000 msec light stimulus duration and then transferred to 15 msec stimulus duration.

Performance was determined based on a rat's calculated VI:

$$VI=(h-f)/[2*(h+f)-(h+f)^2], \text{ wherein}$$

h (relative hits)=#Hits/(#Hits+#Misses), and
f (relative misses)=#False Alarms/(#False Alarms+#Correct Rejections).

VI of 1 indicates complete vigilance; VI of 0.35 indicates above chance vigilance; and VI of −1 indicates no vigilance.

Testing occurred over a 45 min session of randomly presented signal and non-signal trials. Criterion performance required a rat to achieve greater than 59% signal and non-signal trials, a VI greater than 0.35 and less than 25% omissions per day for three consecutive days. Once subjects stabilized at a baseline, their responses are no longer considered random.

SK609 was administered intraperitoneally (IP) at various doses 15 min prior to beginning the task. Prazosin was administered IP 30 min prior, and SK609 15 min prior to beginning the task. Data are presented as difference scores for VI from an average baseline (FIGS. 4-6).

Figure 4:
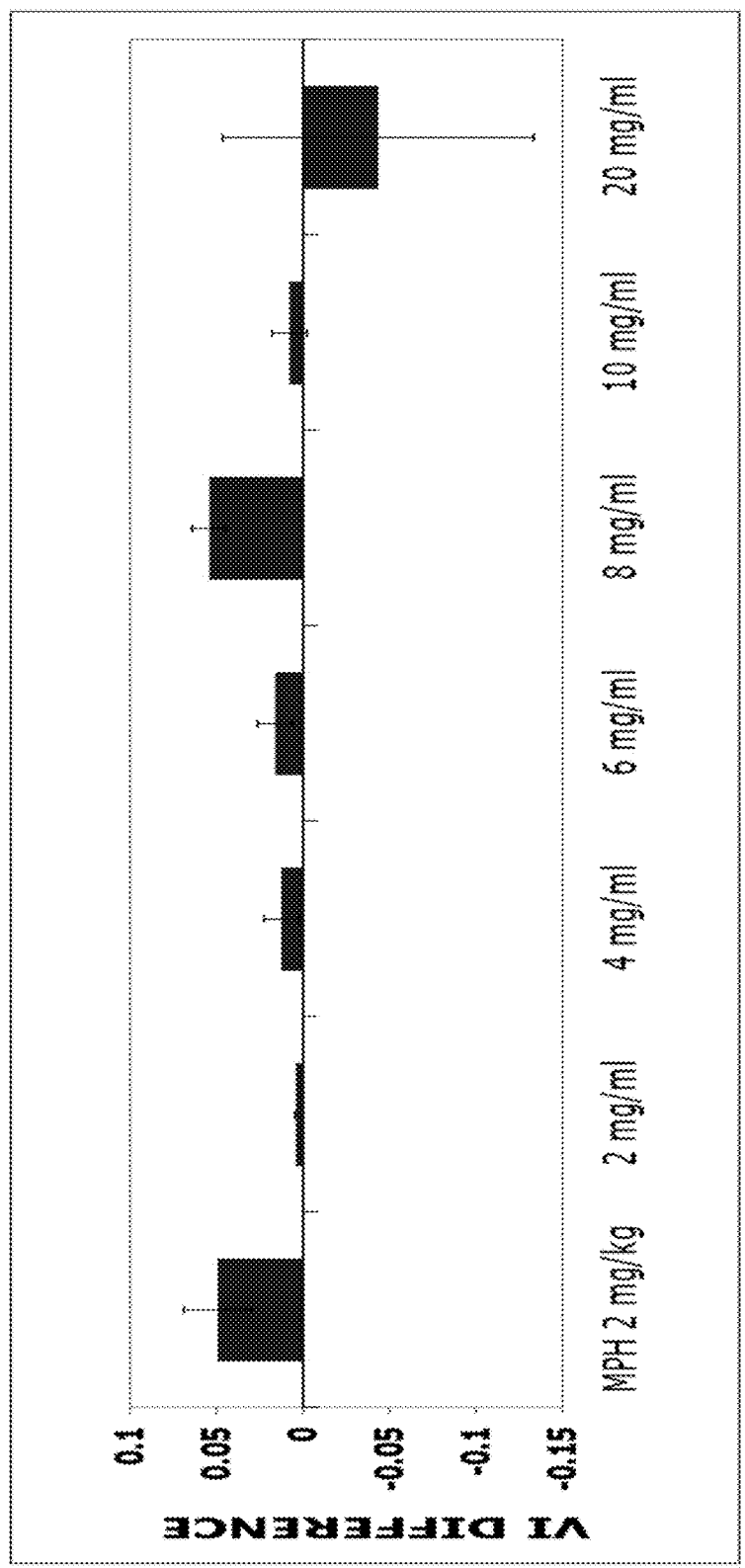
FIG. 4 is a graph illustrating vigilance index (VI) scores against varying doses of SK609 (doses of 2, 4, 8, 10 and 20 mg/kg at 1 ml/kg weight) in a sustained attention task. A typical inverted-U shaped performance was observed with SK609 treatment; a peak dose of 8 mg/kg was completely abrogated by pre-treatment with prozosin and moderately by $D_2$-like antagonist raclopride. The peak dose performance of SK609 was similar to the performance of MPH.
Figure 5:
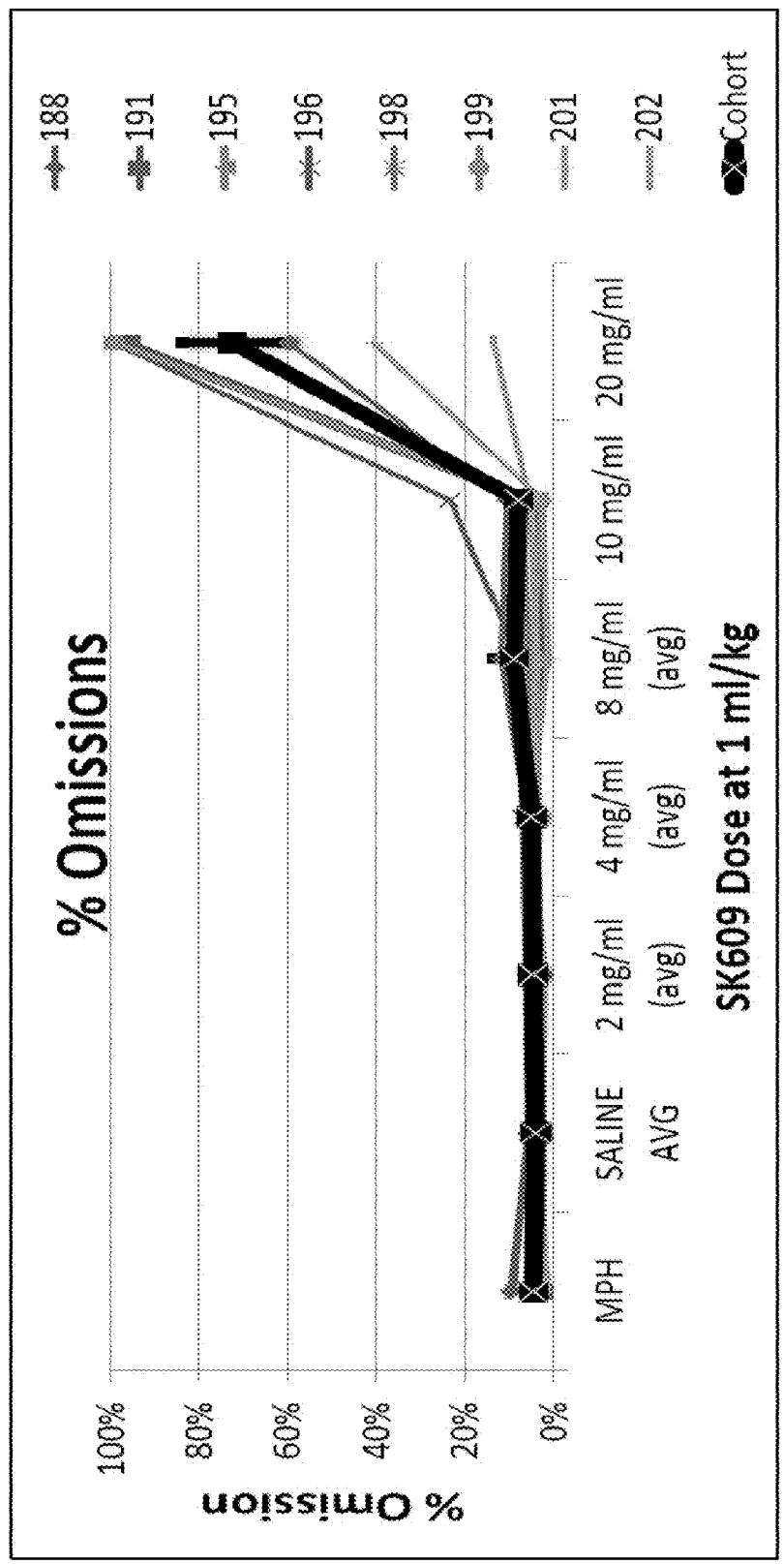
FIG. 5 is a bar graph illustrating the % omission as a function of SK609 dose. IP administration of SK609 at high doses increased the % of omissions for the cohort.
Figure 6:
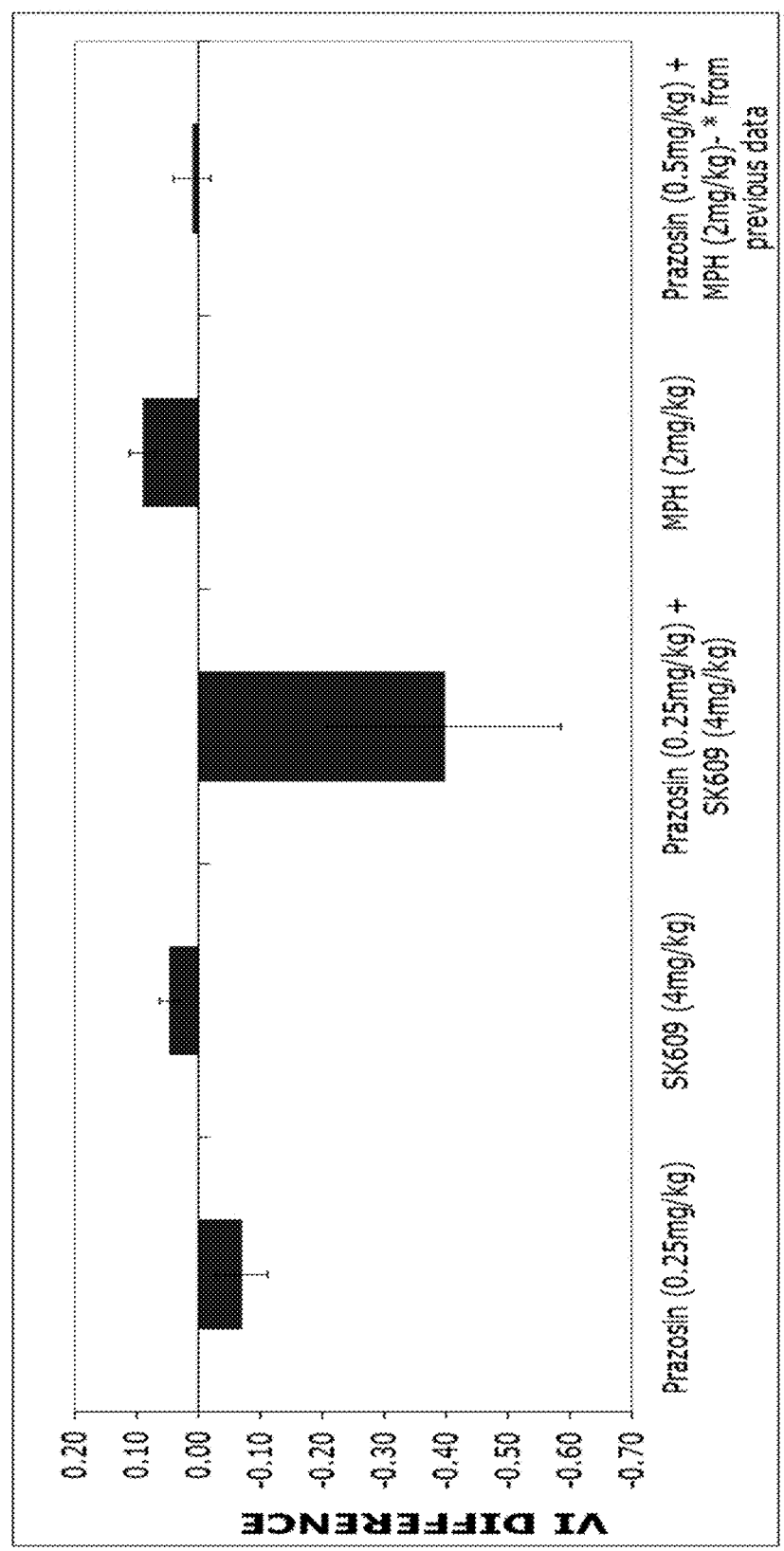
FIG. 6 is a bar graph illustrating the finding that administration of prazosin (IP, 0.25 mg/kg) blocked the effects of administration of SK609 (IP, 4.0 mg/kg) in rats (n=6, *p=0.07). Prazosin had similar blocking effect with MPH administration.

As illustrated in FIGS. 4-5, SK609 enhanced sustained attention at a dose of 8 mg/kg, without increasing omissions. However, higher doses increased omissions. As illustrated in FIG. 6, the α1 adrenergic receptor antagonist prazosin reversed the enhancement of sustained attention, similar to its reversal of MPH.

Taken together, these results indicate that the norepinephrine system is important for sustained attention. In certain embodiments, the effects of SK609 may be assessed through a repetition of doses as well as the use of additional dopamine and norepinephrine antagonists.

The compounds of the present invention may be tested in rodent models for AD and PD. The compounds of the present invention may also be tested for self administration in rodents and conditional place preference tests, which are among the most tested paradigm for drugs of abuse. Additional cognitive models, such as set shifting, five-choice serial reaction time task, radial maze and water maze in healthy and animals with neuronal disorders may also be employed.

Example 2: Prefrontal Cortex (PFC) Mediated Tasks

Catecholamines, particularly norepinephrine and dopamine, strongly modify cognitive functions. As demonstrated herein, in rodent models of cognitive flexibility, SK609 showed no drug effect in the set-shifting task, but improved performance in cross maze. Use of the $D_2/D_3$-like receptor antagonist raclopride still demonstrated ability to inhibit cognitive performance. When these results were compared to previous studies on methylphenidate (Berridge, et al., 2012, Biol. Psych. 71(5):567-73), SK609 performed comparable to MPH in cross-maze but not in set-shifting.

Taken together, our results indicate that PFC-mediated tasks of sustained attention and working memory may be mediated by different mechanisms. Sustained attention appears to be mediated by both norepinephrine and dopamine.

Methods (a) Sustained Attention:

The operant conditioning chambers contained a house light (2.8 W), a stimulus light (2.8 W), a pair of retractable levers and water reward apparatus. Eight water-restricted male Sprague-Dawley rats were trained in an operant task of sustained attention. In response to both signal and non-signal conditions, a water reward was given for correct responses as a positive reinforcer.

Rats were first trained by successive approximation to establish lever pressing behavior. Subsequently, the rats were trained to criterion performance. Criterion performance required a rat to achieve greater than 59% signal and non-signal trials, a VI greater than 0.35 and less than 25% omissions per day for three consecutive days.

MPH (2.0 mg/kg) or SK609 (4.0 mg/kg; this dose for a younger cohort was found to be comparable to the dose of 8.0 mg/kg in older animals) was administered (IP) at various doses 15 min prior to beginning the task. Prazosin (0.25 mg/kg) and raclopride (0.05 mg/kg) were administered (IP) 30 min prior to the experiment followed by either SK609 (4.0 mg/kg) or MPH (2.0 mg/kg) 15 min prior to beginning the task. Performance was determined based on a rat's calculated Vigilance Index (VI). Data are presented as difference scores for VI from an average baseline.

(b) Set-Shifting:

Sixteen food-restricted male Sprague-Dawley rats were trained to discriminate between a pair of small ceramic pots in order to retrieve a food reward buried within one of the pots. A pair of pots differed from each other along three possible dimensions: scent, digging medium, or material covering the outer surface of the pot.

Simple discriminations (SD) were made between pots differing from each other along one dimension. Compound Discriminations (CD) were made between pots differing along two dimensions. Intra-dimensional Shifts (IDS) were changes made within a previously tested dimension. Extra-Dimensional Shifts (EDS) were changes made to a previously untested dimension.

Animals were tested on their ability to form an attentional set by attending to the dimension that predicts the food reward. Animals were then tested on their ability to make an IDS, EDS, or reversal by responding only to the new salient dimension while suppressing the urge to respond to the previously salient stimulus.

0.9% saline (1 mg/kg), raclopride (0.05 mg/kg) or SK609 (4 mg/kg) were administered (IP) 30 prior to the experiment followed by 0.9% saline (1 mg/kg) 15 min prior to beginning the task. Animals were tested to criterion performance of 5 consecutive correct trials.

Figure 7:
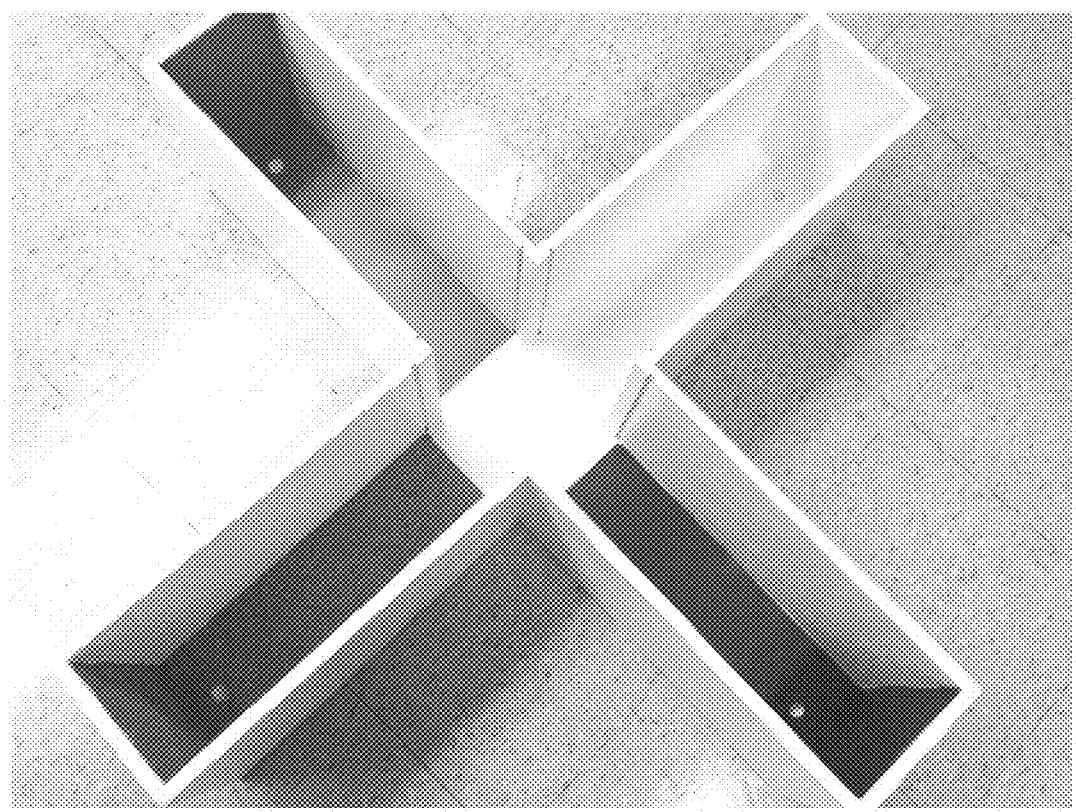
FIG. 7 is an illustration of a cross maze used to test compounds of the present invention.

(c) Cross Maze:

The experimental design for cross maze task was adapted from Stefani et al, 2003, Behav. Neurosci. 117(4):728-37 (FIG. 7). Ten food-restricted male Sprague-Dawley rats were acclimated to a cross maze whose arms differed by color (red vs blue) or texture (smooth vs rough). A food reward was placed in a food well located at the end of the arm.

Rats were trained to form a mental set by associating a food reward with one feature of one dimension. Rats were subsequently tested on their ability to predict the food reward based on one feature of the alternative dimension.

0.9% saline (1 mg/kg), raclopride (0.05 mg/kg) or SK609 (4 mg/kg) were administered (IP) 30 prior to the experiment, followed by 0.9% saline (1 mg/kg) 15 min prior to beginning the task. Animals were tested to criterion performance of 8 consecutive correct trials.

The results of the experiments are now illustrated.

Sustained Attention:

FIG. 4 illustrates the dose-dependent response of SK609, which showed an inverted-U dose response relationship, with a peak dose at 8 mg/kg.

FIG. 6 illustrates the effect of prazosin on SK609 and MPH (as positive control). IP prazosin (0.25 mg/kg) blocked the effects of IP administration of MPH (2.0 mg/kg) in rats (n=8).

Figure 8:
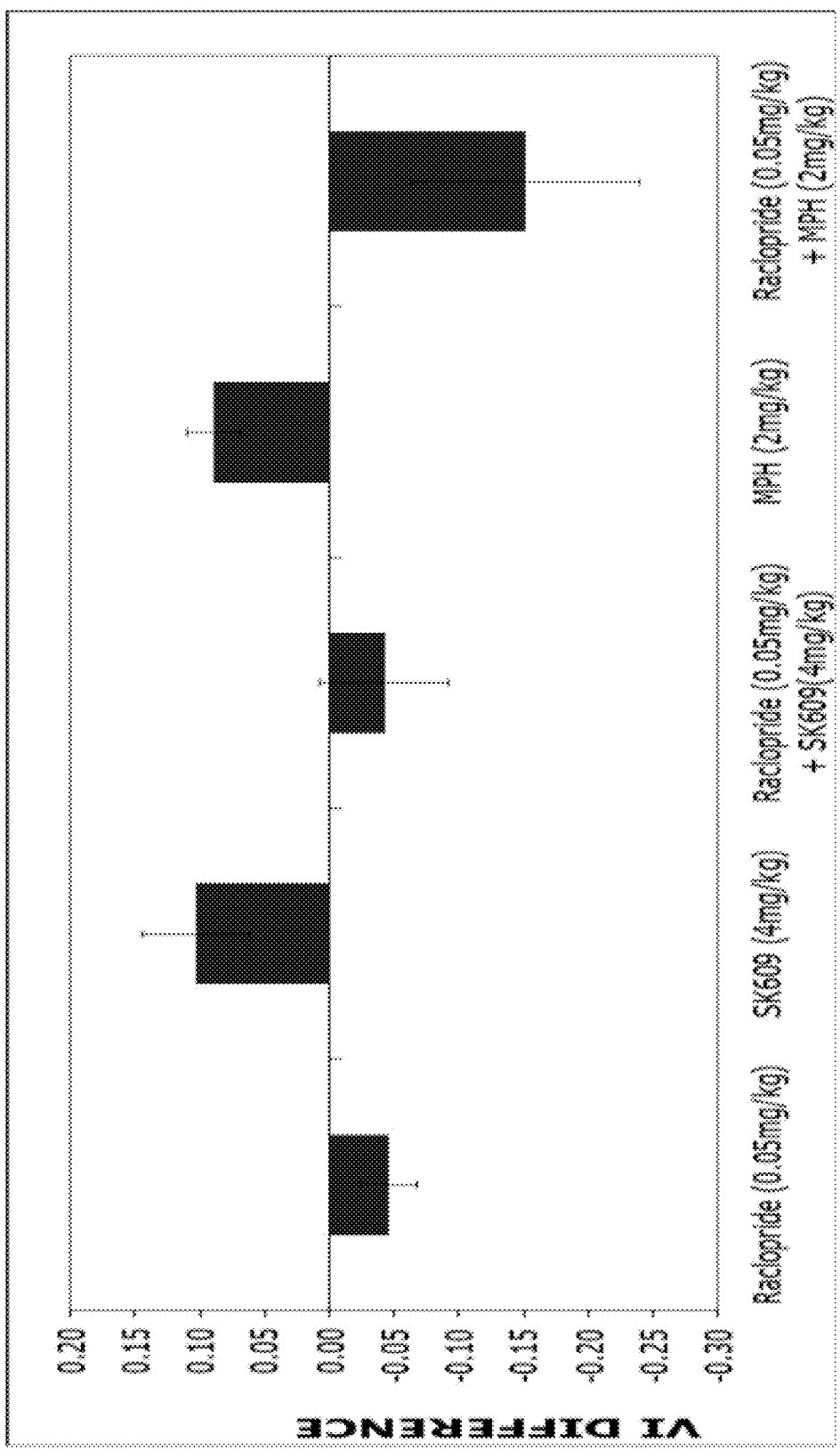
FIG. 8 is a bar graph that illustrates the effect of raclopride on SK609 and MPH in a vigilance index (VI) score experiment.

FIG. 8 illustrates the effect of raclopride on SK609 and MPH (as positive control). IP raclopride (0.05 mg/kg) blocked the effects of IP administration of SK609 (4.0 mg/kg) in rats (n=7).

Figure 9:
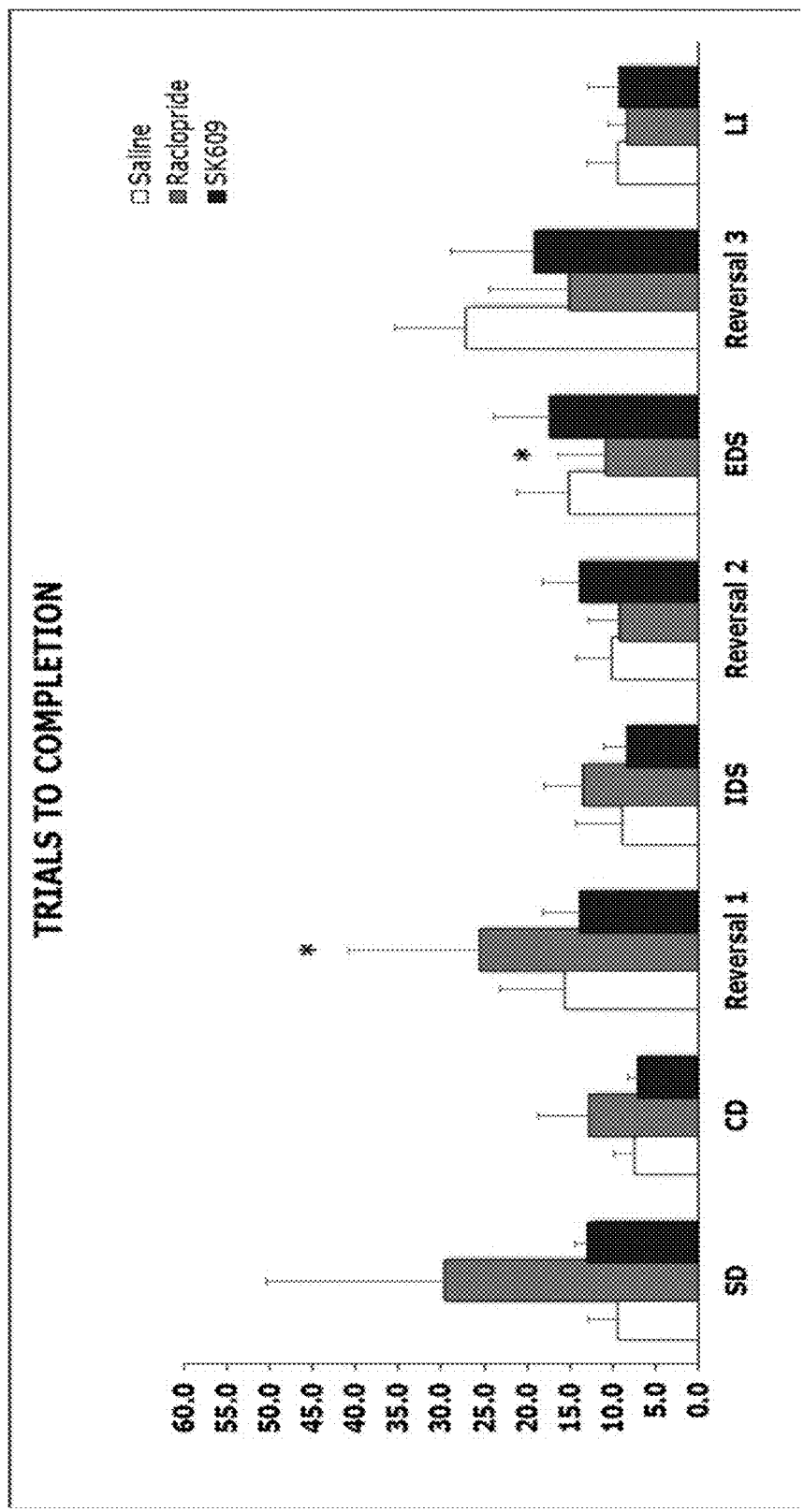
FIG. 9 is a bar graph that illustrates the effect of SK609 and raclopride in a set-shifting task.

Set-Shifting Task:

SK609, a $D_3$ agonist and NET inhibitor that improves cognitive performance in sustained attention, was used to test the roles of catecholamines in cognitive flexibility using the set-shifting task. Rats (n=4) given IP administration of SK609 (4.0 mg/kg) did not differ significantly from saline (n=4) in Extra-Dimensional Shifts (EDS), Intra-Dimensional Shifts (IDS), or compound discriminations (CD) (FIG. 9). Additionally, rats (n=8) given IP injections of the $D_2/D_3$ antagonist raclopride (0.05 mg/kg) demonstrated impairments in performance relative to controls (p-value=0.04).

Figure 10A:
FIGS. 10A-10B, illustrates the effect of SK609 in a cross-maze task.
Figure 10B:
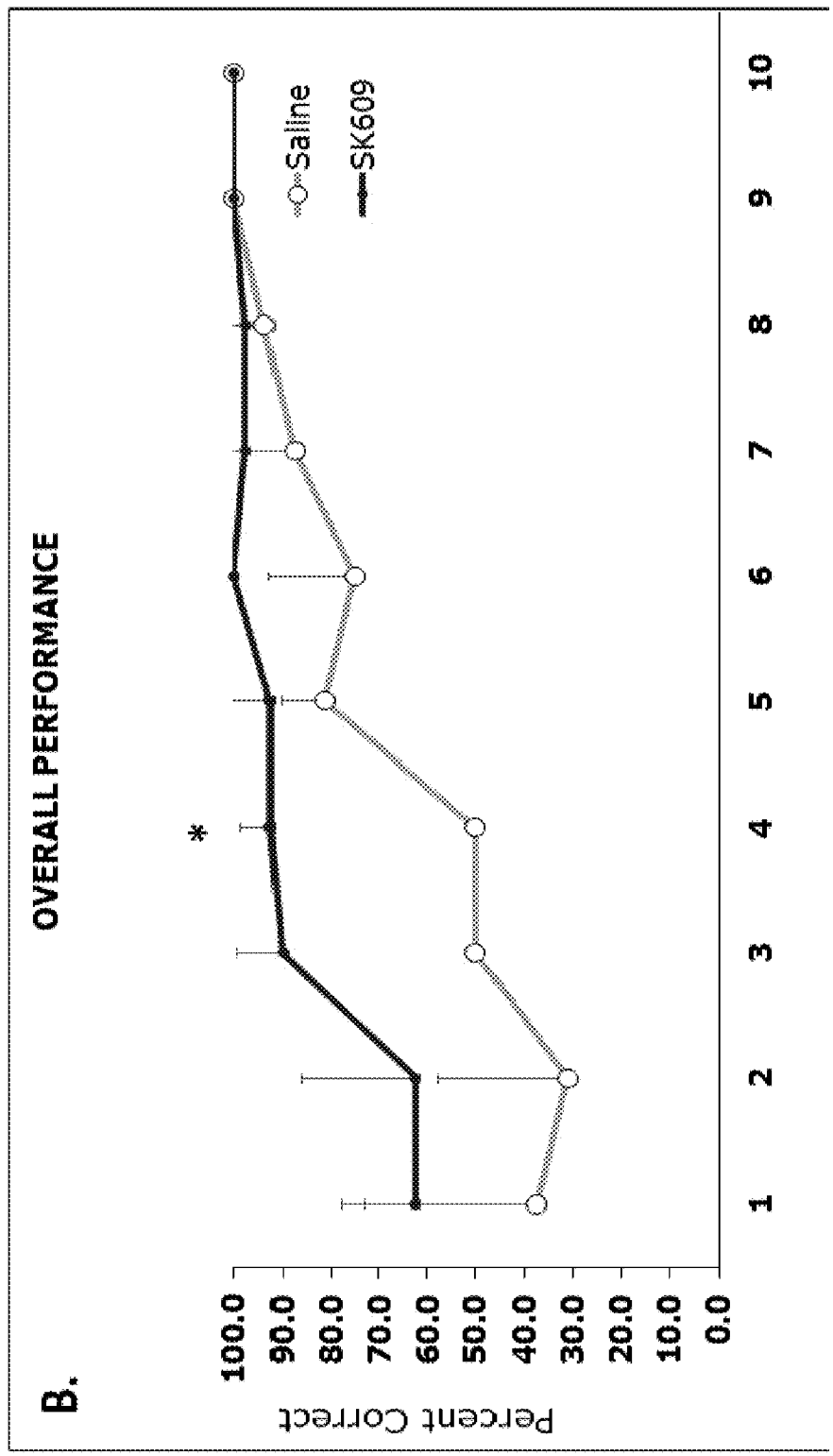

Cross-Maze:

Effects seen in set-shifting were tested in the Cross Maze, an alternative to task that also tests cognitive flexibility. In this task, IP administration of SK609 (4.0 mg/kg) in rats (n=5) improved performance relative to saline (n=2) (p-value=0.027) (FIG. 10A). Performance was analyzed in 8 trial increments over a total of 80 trials. SK609 improved performance faster and maintained improvements better than saline (p-value=0.008) (FIG. 10B).

Taken together, the present results indicated that sustained attention is mediated by both dopamine and norepinephrine. SK609-enhanced performance was reversed by pretreatment with the $D_2/D_3$ antagonist raclopride, suggesting a role for DA in PFC-mediated cognition. SK609-enhanced performance was reversed by pretreatment with the α adrenergic receptor antagonist prazosin, but an increase in omissions was also observed. In models of cognitive flexibility, SK609 did not enhance performance in set-shifting tasks, but showed significant improvement in cross-maze.

Different molecular mechanisms may govern cognitive flexibility and sustained attention. The mechanisms governing sustained attention involves both norepinephrine and dopamine.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the present invention. The appended claims are intended to be construed to include all such embodiments and equivalent variations.

What is claimed is:

1. A method of treating attention deficit disorder (ADD) or attention deficit hyperactivity disorder (ADHD) in a subject in need thereof, the method comprising administering to the subject a therapeutically effective amount of a compound of formula (I):

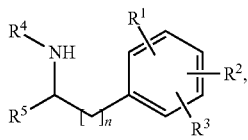

wherein:
$R^1$, $R^2$ and $R^3$ are independently selected from the group consisting of H, cyano, hydroxyl, halo, alkoxy, nitro, $C_{1-6}$ alkyl, and carboxy;
$R^4$ is selected from the group consisting of H and $C_{1-6}$ alkyl;
$R^5$ is selected from the group consisting of H, $C_{1-6}$ alkyl, and substituted $C_{1-6}$ alkyl; and,
n is 2;
a pharmaceutically acceptable salt or solvate thereof, and any mixtures thereof.

2. The method of claim 1, wherein administration of the compound improves sustained attention in the subject.

3. The method of claim 1, wherein in formula (I) $R^1$, $R^2$ and $R^3$ are independently selected from the group consisting of H, halo, alkoxy, and $C_{1-6}$ alkyl.

4. The method of claim 1, wherein in formula (I) $R^5$ is selected from the group consisting of H, and $C_{1-6}$ alkyl.

5. The method of claim 1, wherein the at least one compound is selected from the group consisting of: 2-amino-4-(2-chlorophenyl)butan-1-ol; 2-(3-aminohexyl)phenol; 4-(2-chlorophenyl)-2-methylamino-butane; 4-(2-chlorophenyl)-butan-2-amine; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl)phenol; 3-(3,4-diethoxyphenyl)propan-1-amine; 4-(4-chlorophenyl)butan-2-amine; 4-(4-methoxyphenyl)butan-2-amine; a pharmaceutically acceptable salt or solvate, and mixtures thereof.

6. The method of claim 1, wherein the composition further comprises at least one drug selected from the group consisting of methylphenidate, dextroamphetamine, dextroamphetamine-amphetamine, lisdexamfetamine, an additional compound that is used to treat ADHD, antidepressant, clonidine, guanfacine, and a salt or solvate thereof.

7. The method of claim 1, wherein the subject is human.

8. A method of treating dementia associated with a neurodegenerative disease in a subject in need thereof, wherein the neurodegenerative disease comprises at least one selected from the group consisting of Alzheimer's Disease (AD), Huntington's Disease, transmissible spongiform encephalopathies (TSEs), chronic traumatic encephalopathy (CTE) resulting from repeated traumatic brain injuries, and amyotrophic lateral sclerosis (ALS), the method comprising administering to the subject a therapeutically effective amount of a compound of formula (I):

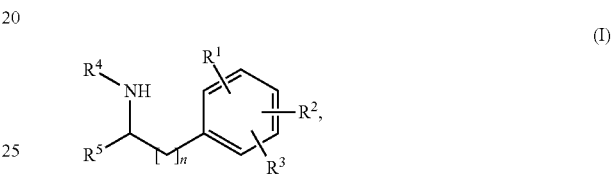

wherein:
$R^1$, $R^2$ and $R^3$ are independently selected from the group consisting of H, cyano, hydroxyl, halo, alkoxy, nitro, $C_{1-6}$ alkyl, and carboxy;
$R^4$ is selected from the group consisting of H and $C_{1-6}$ alkyl;
$R^5$ is selected from the group consisting of H, $C_{1-6}$ alkyl, and substituted $C_{1-6}$ alkyl; and,
n is 2;
a pharmaceutically acceptable salt or solvate thereof, and any mixtures thereof.

9. The method of claim 8, wherein in formula (I) $R^1$, $R^2$ and $R^3$ are independently selected from the group consisting of H, halo, alkoxy, and $C_{1-6}$ alkyl.

10. The method of claim 8, wherein in formula (I) $R^5$ is selected from the group consisting of H and $C_{1-6}$ alkyl.

11. The method of claim 8, wherein the at least one compound is selected from the group consisting of: 2-amino-4-(2-chlorophenyl)butan-1-ol; 2-(3-aminohexyl)phenol; 4-(2-chlorophenyl)-2-methylamino-butane; 4-(2-chlorophenyl)-butan-2-amine; 4-(2-fluorophenyl)butan-2-amine; 4-(2-bromophenyl)butan-2-amine; 4-(2-iodophenyl)butan-2-amine; 4-(2-methoxyphenyl)butan-2-amine; 2-(3-aminobutyl) phenol; 3-(3,4-diethoxyphenyl)propan-1-amine; 4-(4-chlorophenyl)butan-2-amine; 4-(4-methoxyphenyl)butan-2-amine; a pharmaceutically acceptable salt thereof, and any mixtures thereof.

12. The method of claim 8, wherein the composition further comprises at least one drug selected from the group consisting of methylphenidate, dextroamphetamine, dextroamphetamine-amphetamine, lisdexamfetamine, an additional compound that is used to treat ADHD, antidepressants, clonidine, guanfacine, and a salt or solvate thereof.

13. The method of claim 8, wherein the subject is human.

* * * * *

UNITED STATES PATENT AND TRADEMARK OFFICE
CERTIFICATE OF CORRECTION

PATENT NO. : 9,861,594 B2
APPLICATION NO. : 15/028654
DATED : January 9, 2018
INVENTOR(S) : Sandhya Kortagere It is certified that error appears in the above-identified patent and that said Letters Patent is hereby corrected as shown below:

In the Claims

In Column 26, Lines 1-2, Claim 6 "the composition further comprises" should read as follows:
-- the compound is administered as a composition further comprising --;

In Column 26, Lines 56-57, Claim 12 "the composition further comprises" should read as follows:
-- the compound is administered as a composition further comprising --.

Signed and Sealed this
Thirtieth Day of March, 2021

Drew Hirshfeld
*Performing the Functions and Duties of the
Under Secretary of Commerce for Intellectual Property and
Director of the United States Patent and Trademark Office*